(12) United States Patent
Schwamm et al.

(10) Patent No.: US 6,542,769 B2
(45) Date of Patent: Apr. 1, 2003

(54) IMAGING SYSTEM FOR OBTAINING QUANTATIVE PERFUSION INDICES

(75) Inventors: Lee H. Schwamm, Newton, MA (US); A. Gregory Sorensen, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 226 days.

(21) Appl. No.: 09/739,194

(22) Filed: Dec. 18, 2000

(65) Prior Publication Data

US 2002/0111550 A1 Aug. 15, 2002

(51) Int. Cl.$^7$ ................................................. A61B 5/05
(52) U.S. Cl. ...................................... 600/420; 600/410
(58) Field of Search ................................. 600/420, 407, 600/410, 419, 310, 317, 458, 481, 504, 505

(56) References Cited

U.S. PATENT DOCUMENTS

| | | | |
|---|---|---|---|
| 4,316,391 A | | 2/1982 | Tickner |
| 4,873,989 A | | 10/1989 | Einzig |
| 4,874,949 A | | 10/1989 | Harris et al. |
| 5,231,464 A | | 7/1993 | Ichimura et al. |
| 5,437,274 A | | 8/1995 | Khoobehi et al. |
| 5,443,071 A | | 8/1995 | Banjanin et al. |
| 5,551,435 A | * | 9/1996 | Sramek ........................ 600/481 |
| 5,579,767 A | | 12/1996 | Prince ........................ 128/65 |
| 5,723,104 A | | 3/1998 | Fung et al. |
| 5,766,127 A | * | 6/1998 | Pologe et al. ................ 600/310 |
| 5,792,057 A | | 8/1998 | Rubsamen et al. |
| 5,845,639 A | | 12/1998 | Hochman et al. |
| 5,860,922 A | | 1/1999 | Gordon et al. |
| 5,900,228 A | | 5/1999 | Meade et al. ................ 424/9.3 |
| 5,928,625 A | | 7/1999 | Dorshow et al. |
| 5,952,664 A | | 9/1999 | Wake et al. |
| 5,954,658 A | | 9/1999 | Gorti |
| 5,976,502 A | | 11/1999 | Khoobehi et al. |
| 5,983,120 A | | 11/1999 | Groner et al. |
| 6,123,921 A | | 9/2000 | Meade et al. ................ 424/9.3 |
| 6,292,683 B1 | * | 9/2001 | Gupta et al. ................ 600/410 |

FOREIGN PATENT DOCUMENTS

WO        98/08434        3/1998

OTHER PUBLICATIONS

IC–GREEN™; "Sterile Indocyanine Green"; Manufactured for Akorn, Inc.; pp. 1–6.

Leif Ostergaard et al.; "High Resolution Measurement of Cerebral Blood Flow Using Intravascular Tracer Bolus Passages. Part II: Experimental Comparison and Preliminary Results."; MRM 36; pp. 726–736 (1996).

Leif Ostergaard et al.; "High Resolution Measurement of Cerebral Blood Flow Using Intravascular Tracer Bolus Passages. Part I: Mathematical Approach and Statistical Analysis"; MRM 36; pp. 715–725 (1996).

P. Lund–Johansen; "The Dye Dilution Method for Measurement of Cardiac Output" European Heart Journal (1990) II (Supplement I); pp. 6–12.

(List continued on next page.)

Primary Examiner—Teresa Walberg
Assistant Examiner—Quang T Van
(74) Attorney, Agent, or Firm—Daly, Crowley & Mofford, LLP

(57) ABSTRACT

A bolus containing optical and MRI contrast agents is administered to a patient for determining quantitative perfusion indices from perfusion weighted magnetic resonance imaging analysis (PWI). The optical contrast agent time-concentration data, which can be obtained non-invasively, is used to define an arterial input function. The MRI contrast agent time concentration can be non-invasively determined using MRI to define a tissue function. An MRI time-signal curve can be determined by deconvolving the arterial and tissue functions. In one embodiment, SVD is used to determine a residue function from which a flow map can be computed.

17 Claims, 4 Drawing Sheets

OTHER PUBLICATIONS

Sung–cheng Huang et al.; "Chapter 7—Principles of Tracer Kinetic Modeling in Positron Emission Tomography and Autoradiography"; Positron Emission Tomography and Autoradiography: Principles and Applications for the Brain and Heart; Edited by M. Phelps, J. Mazziotta and H. Schelbert; Raven Press; New York; 1986; pp. 287–346.

Edward J. Hoffman et al.; "Chapter 6—Positron Emission Tomography: Principles and Quantitation"; Positron Emission Tomography and Autoradiography: Principles and Applications for the Brain and Heart; Edited by M. Phelps, J. Mazziotta and H. Schelbert; Raven Press; New York; 1986; pp. 237–286.

* cited by examiner

IMAGING SYSTEM FOR OBTAINING QUANTATIVE PERFUSION INDICES

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates generally to imaging systems, and more particularly, to imaging systems for imaging physiological functions.

BACKGROUND OF THE INVENTION

Measuring blood flow within the body can be a useful tool in diagnosing and treating patients. As known to one of ordinary skill in the art, certain organs in the body, such as the brain and heart, are damaged relatively quickly without an adequate flow of blood. The amount of blood flow can be an important factor in determining the optimal treatment option for a patient.

There are a variety of known systems for obtaining blood flow information from various locations in the body, such as the brain. One technique for obtaining quantitative blood flow information is Positron Emission Tomography (PET). PET is not widely used due to several practical and medical disadvantages. For example, PET systems are relatively expensive to operate and require the use of a cyclotron, which is not generally available. In addition, PET requires the use of radionucleotides, which are potentially harmful to a patient. Furthermore, the anatomical resolution of PET is limited, i.e., significantly less than Magnetic Resonance Imaging (MRI).

Another technique for measuring blood flow is known as Xenon enhanced CT (computed tomography). Like PET, Xenon-enhanced CT can be uncomfortable to the patient, exposes the patient to ionizing radiation, and is limited in anatomical resolution.

Another known technique for obtaining blood flow information is known as perfusion weighted Magnetic Resonance Imaging (MRI) or PWI. In general, MRI systems provide a relatively high degree of anatomical resolution. A common type of PWI relies upon the temporal characteristics of a paramagnetic chelate, such as a gadolinium derivative, delivered as a bolus intravascularly. The chelate functions as a contrast agent for monitoring the signal intensity of the vasculature. In general, the signal intensity decreases relative to the surrounding tissue, which serves as the basis to image the tissue. If the vasculature is intact in the region of interest, e.g., for the brain there is no leakiness in the blood-brain barrier, the signal drop can be used to image the blood flow in the brain. Image analysis over time can be used to determine relative differences in blood volume, flow, and mean transit time.

While PWI can be used to compare relative blood flows at different locations, such as on left and right sides of the brain, this information may be of limited utility. For example, PWI can identify a problem in the case where one side of the brain has one half the blood flow of the other side of the brain. However, if both sides of the brain have half the normal blood flow this reduction in flow may not be identified.

FIG. 1 shows an artery 2 providing blood to a region of tissue, such as a capillary bed 4, within an organ 6. In a common form of PWI, the natural logarithm of the signal change in the tissue is estimated to be proportional to the concentration of the MRI contrast agent, when a T2 contrast agent and appropriate MRI parameters are used. (A different mathematical relationship between contrast agent concentration and MRI signal change is present with other types of contrast agents such as T1-based agents.) However, the signal change may not be proportional to MRI contrast agent concentration in larger blood vessels. Thus, an MRI-derived arterial input function (AIF) provides limited ability to determine quantitative blood perfusion indices. That is, PWI is generally limited to providing relative perfusion information due to the nonlinear nature of the signal change in relatively large blood vessels.

It would, therefore, be desirable to provide a minimally invasive technique for determining quantitative perfusion indices with relatively high anatomical resolution without the injection of harmful agents or the use of ionizing radiation.

SUMMARY OF THE INVENTION

The present invention provides a method for determining quantitative perfusion indices using magnetic resonance imaging (MRI) and optical densitometry. In general, a bolus containing an MRI contrast agent (tracer) and an optical contrast agent is injected into a patient. MRI is used to determine tracer concentration in a tissue volume of interest (VOI) and optical densitometry is used to determine the arterial input function. Using deconvolution, quantitative blood flow information can be determined.

In one aspect of the invention, a bolus containing an optical contrast agent and an MRI contrast agent is administered to a patient. Optical contrast agent concentration is sampled over time, such as by optical densitometry or fluoresence to derive an arterial input function. The concentration-time curve of the MRI contrast agent is determined using MRI to derive a tissue function. The optical and MRI contrast agents are sampled at known times such that the samples can be correlated in time. From the known relationship between the MRI and optical contrast agents in the bolus, quantitative blood flow information can be derived using deconvolution.

In a further aspect of the invention, a solution containing an optical contrast agent and an MRI contrast agent is provided. In one embodiment, the optical contrast agent includes Indocyanine Green (ICG) and the MRI contrast agent includes gadopentate dimegluminepentaacetic acid (Gd-DTPA), also known by the trade name Magnevist. The solution can be used as a bolus injection to determine quantitative blood flow information from optical and MRI time-concentration data.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a technique for obtaining quantitative maps of blood perfusion indices from perfusion weighted magnetic resonance imaging (MRI) or PWI. In general, a mixture of an optical contrast agent and an MRI contrast agent is produced. This optical/paramagnetic bolus is injected into the patient. The optical agent concentration is monitored using optical densitometry (or fluorometry) and the MRI contrast agent, for example a paramagnetic agent, concentration is monitored using MRI. By correlating the optical and paramagnetic concentrations in time, PWI can provide potentially absolute quantitative blood flow information in contrast to conventional PWI analysis that provides only relative perfusion information.

Figure 1:
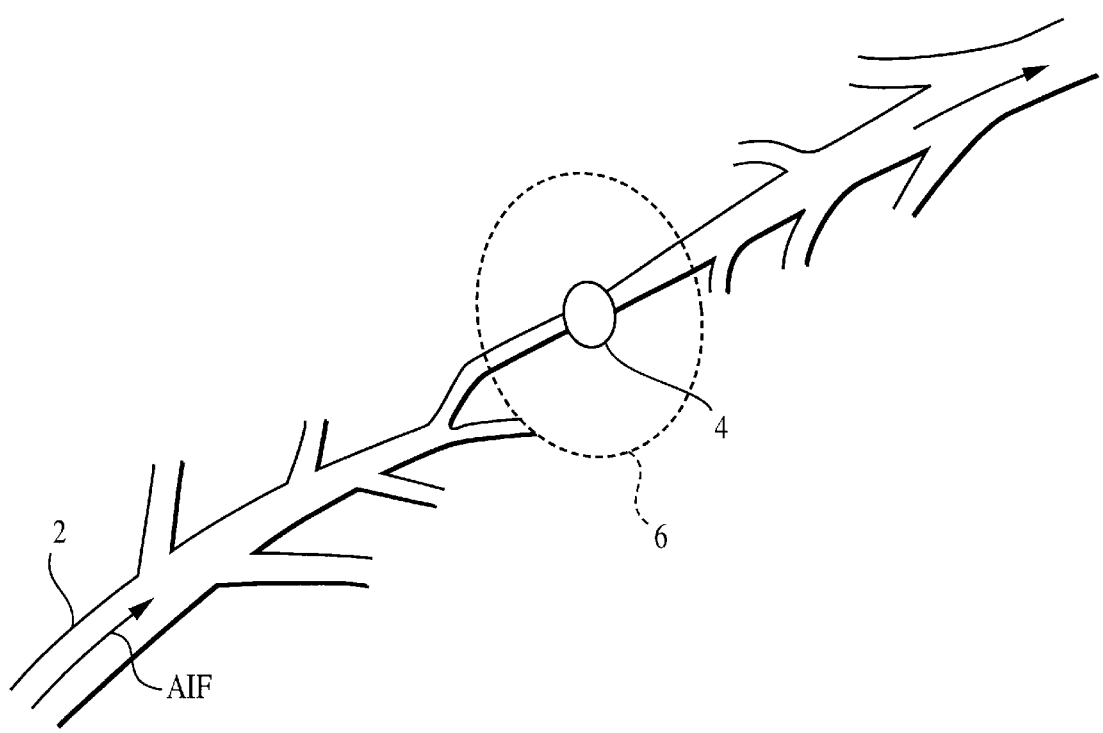
FIG. 1 is pictorial representation of a blood flow from an artery into a capillary bed as known in the prior art.
Figure 2:
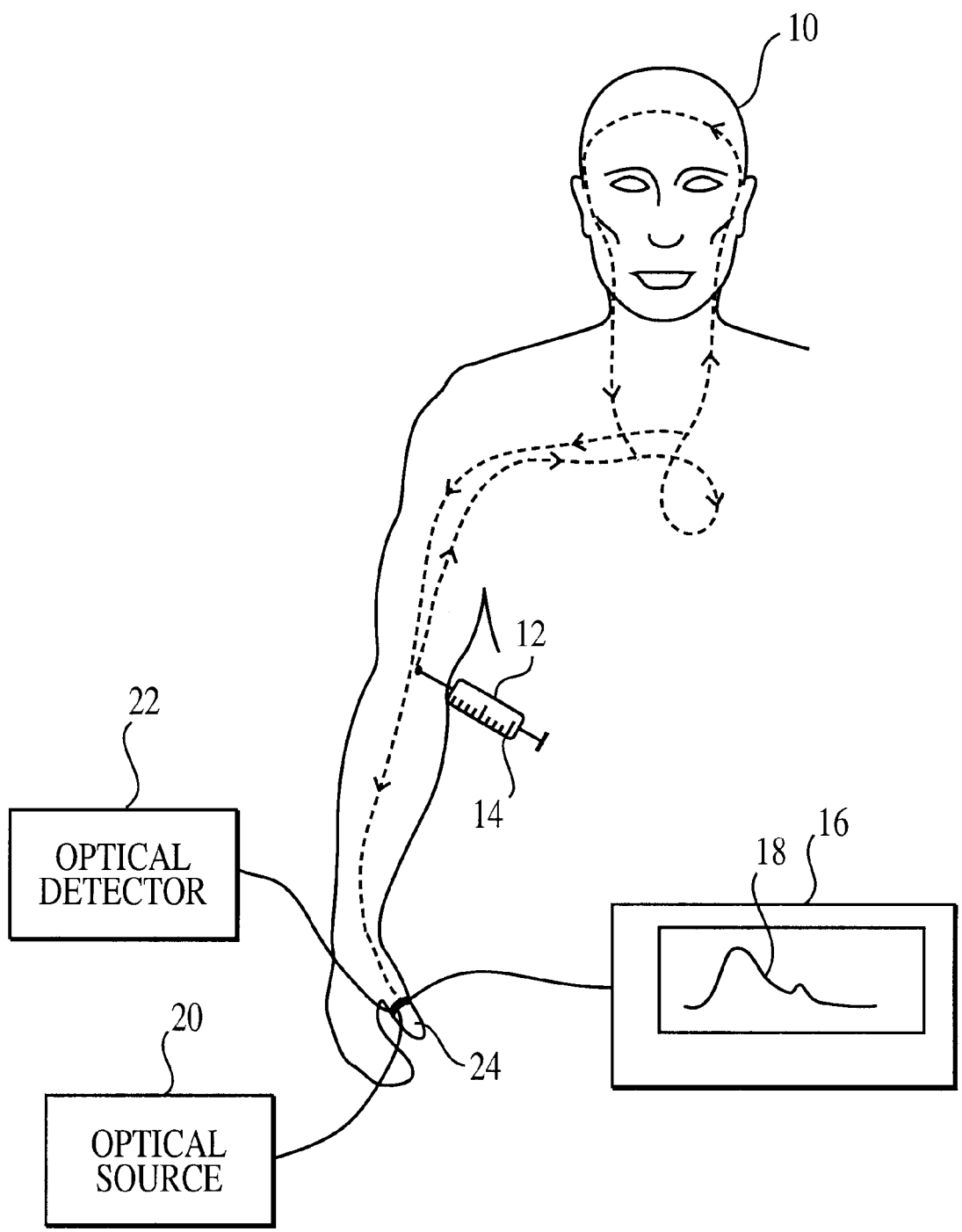
FIG. 2 is a pictorial representation of a patient receiving an optical/MRI contrast agent bolus in accordance with the present invention.

FIG. 2 shows a patient 10 receiving an optical/paramagnetic bolus 12 via a needle 14 in accordance with the present invention. The patient 10 can be coupled to a conventional optical densitometry device 16 for non-invasively monitoring the concentration-time curve 18 for the optical contrast agent. In one embodiment, the bolus solution 12 includes Indocyanine Green (ICG) as the optical contrast agent and gadopentate dimegluminepentaacetic acid (GDA) as the MRI contrast agent. An exemplary solution comprises 0.125 mg/ml ICG and 457.3 mg mg/ml Gd-DTPA. Injection ranges might be from 0.01 to 1.0 mmol/kg of Gd-DTPA, at injection rates from 0.01 cc/second to 5 cc/second, and a range of ICG injection amount of 0.01 mg/ml to 50 mg/ml.

The optical measurement device 16 provides non-invasive in vivo in situ ICG measurements. More particularly, the device 16 includes an optical source 20 and a detector array 22 positioned on the patient's arm, thumb 24, or other location in, on, or near the patient 10. The optical source 20, e.g., a laser, emits light at a predetermined wavelength or range of wavelengths. The emitted light scatters through the bodily tissue and is detected by the detector array 22. The tissue can be sampled at predetermined times in relation to the time at which the bolus was injected. Since biological chromophores generally have relatively low absorption at about 810 nanometers, the presence of ICG causes a measurable decrease in the detected signal.

In one embodiment, the ICG fluorescence characteristics are used to increase the signal-to-noise ratio. For example, ICG excites at 805 nm and emits at 835 nm. A light source 20 that emits light at a wavelength of about 805 nm and a detector 22 that selectively detects light at 835 nm detects light emitted by the ICG. It is understood that the exact excite and emit wavelengths for ICG can be altered by other elements in the solution, including the paramagnetic agent.

In an alternative embodiment, the patient's blood is sampled at known intervals and the ICG concentration is measured from the blood. For example, the blood samples can be analyzed using laser fluorescence spectroscopy.

Figure 3:
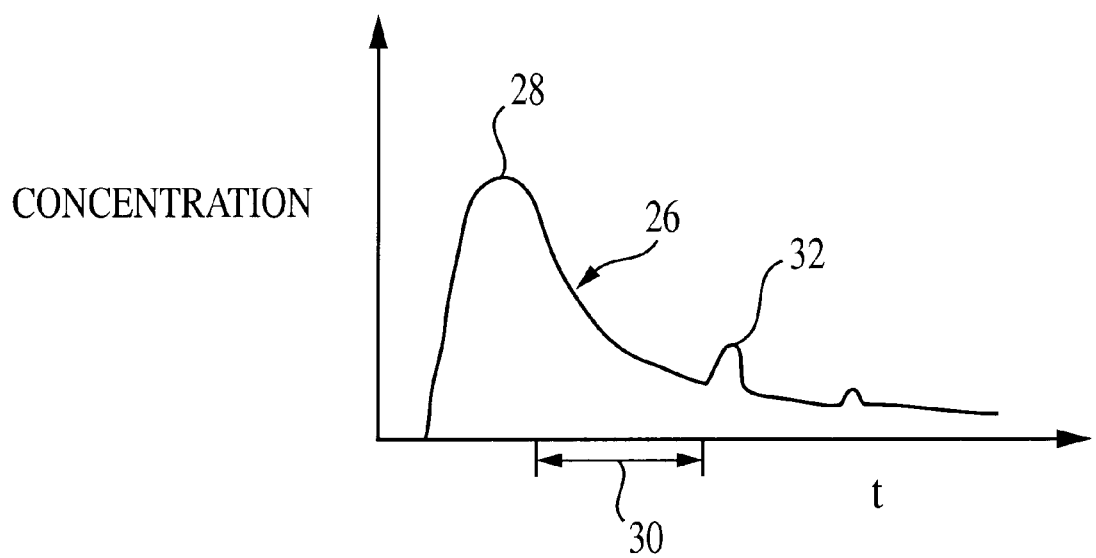
FIG. 3 is a graphical depiction of a time-concentration curve after administration of the optical/MRI contrast bolus in accordance with the present invention.

FIG. 3 is an exemplary time-concentration curve 26 of the optical contrast agent after injection of the bolus 12. As can be seen, immediately after the solution is administered the concentration peaks at point 28 and rapidly declines for a period of time 30 until a concentration spike or echo 32 may occur due to the solution re-circulating. The concentration of the optical contrast agent then typically will gently taper off.

The optical contrast agent time-concentration curve is used to define the arterial input function $C_a(t)$ for the patient. The arterial input function provides a measure of the rate of arterial blood flow through a given artery, which can then be used to correct for any delay or dispersion of the bolus as it progresses to the tissue.

The Gd-DTPA time-concentration curve for a tissue volume of interest (VOI) is determined using MRI in a conventional manner. The GDA time-concentration curve is used to define a tissue function $C_{VOI}(t)$, which is correlated in time with the concentration of the optical contrast agent.

The MR signal-time curve is then deconvolved using the arterial input function $C_a(t)$ and the tissue function $C_{VOI}(t)$ to provide quantitative perfusion data. The MR signal-time curve can be used to generate a flow map for regions of interest. In addition, other maps of hemodynamics can be generated, such as maps of blood volume, tissue mean transit time, and/or other parameters.

Figure 4:
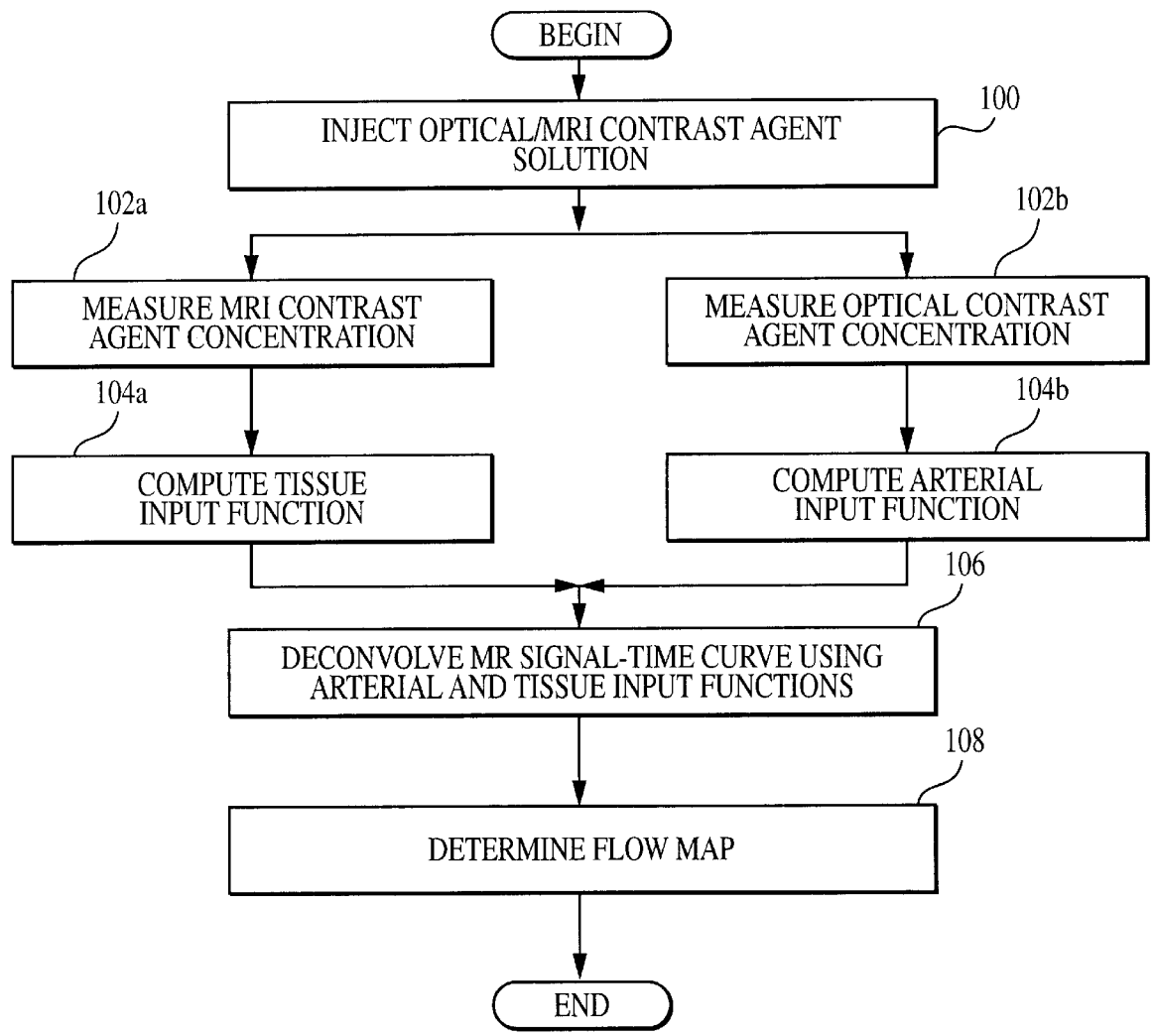
FIG. 4 is a flow chart of an exemplary sequence of steps for determining quantitative perfusion from an arterial input function and a tissue function in accordance with the present invention.

FIG. 4 shows an exemplary sequence of steps for obtaining quantitative perfusion indices in accordance with the present invention. In step 100, an optical/paramagnetic bolus in injected into a patient in accordance with a predetermined protocol, such as the protocol described above. In step 102a, an MRI system is used to determines signal changes in the tissue VOI from the paramagnetic contrast agent concentration. Using magnetic resonance imaging to determine signal changes in tissue using a paramagnetic contrast agent is well known to one of ordinary skill in the art. The signal changes in the tissue are sampled at known times in relation to the time of bolus injection or other reference point. In step 104a, the tissue function $C_{VOI}(t)$ is estimated from the measured signal changes in the tissue VOI in a conventional manner.

Concurrently with measuring signal changes in the tissue (step 102a), optical densitometry, fluorometry, or blood sampling is used to determine the time-concentration curve for the optical contrast agent in step 102b, as described above. In step 104b, the optical agent time-concentration curve is used to estimate the arterial input function $C_a(t)$. Estimating the arterial input function from the optical contrast agent time-concentration curve is well known to one of ordinary skill in the art.

In step 106, the MR signal-time curve is deconvolved using the estimated tissue function and arterial input function to compute the residue function, which can then be used to compute a flow map for the tissue of interest. In an exemplary embodiment, and as described more fully below, the MR signal-time curve is deconvolved as set forth in Equation 1:

$$C_{VOI}(t) = F_t \int_0^t C_a(\tau) R(t-\tau) d\tau \qquad \text{Eq. (1)}$$

where $C_{VOI}(t)$ represents the tissue function, F(t) represents blood flow in the tissue of interest, $C_a(t)$ represents the arterial input function, and R(t) represents the residue function.

In step 108, the flow map for the target tissue is computed from the deconvolved residue function. The flow map can be displayed to show absolute blood flow rates in regions of interest for the patient. The blood flow information can be used to diagnose and treat patients.

In general, the MR signal-time curve is deconvolved from the arterial input function $C_a(t)$, which is derived from optical measurements, with or without MRI measurements, and the tissue function $C_{VOI}(t)$, which is derived from MRI, as shown in Equation (1). A bolus containing a nondiffusable tracer along with the optical contrast agent is injected into a feeding vessel at time t=0. The tracer ultimately reaches a volume of interest (VOI) of tissue through which the tracer particles follow different paths. The transit times through the VOI have a distribution characteristic of the flow and the vascular structure. The probability density function of the transit times is denoted h(t). For an arterial input function $C_a(t)$ given to the tissue VOI, the tracer concentration in the venous output $C_v(t)$ is defined by Equation (2) below:

$$C_v(t) = C_a(t) \otimes h(t) = \int C_a(\tau) h(t-\tau) d\tau \qquad \text{Eq.(2)}$$

where $\otimes$ denotes convolution. In the capillaries, the assumptions regarding the change in MRI signal with concentration of the MRI contrast agent generally hold; however, these assumptions begin to break down in larger vessels due to other effects such as flow-related signal change, bulk susceptibility effects, and the like. As a result, the arterial input function $C_a(t)$ might more accurately be characterized with an optical measurement than with an MRI measurement, since the optical measurement is typically not dependent on vessel size or vessel orientation as is the MRI signal change.

The mean transit time (MTT) for the tracer particles can be defined in terms of the density function as set forth below in Equation (3) below:

$$MTT = \frac{\int_{-\infty}^{\infty} \tau h(\tau) d\tau}{\int_{-\infty}^{\infty} h(\tau) d\tau} \qquad \text{Eq. (3)}$$

The amount of intravascular tracer in the VOI can be determined from the relationship set forth below in Equation (4):

$$CBV = \frac{\int_{-\infty}^{\infty} C_{VOI}(\tau) d\tau}{\int_{-\infty}^{\infty} C_a(\tau) d\tau} \qquad \text{Eq. (4)}$$

For full blood flow and a macrovascular to microvascular hemacrit ratio of about two thirds, the so-called central volume theorem states that the relationship between cerebral blood volume (CBV) and MTT can be defined as stated in Equation (4) below:

$$MTT = \frac{CBV}{F_t} \qquad \text{Eq. (4)}$$

And the fraction of injected tracer present in the vasculature at time t is described by the residue function defined below in Equation (5):

$$R(t) \equiv \left[ 1 - \int_0^t h(\tau) d\tau \right] \qquad \text{Eq. (5)}$$

Since h(t) is defined as a probability density function, R(0)=1 and R(t) is a positive, decreasing function of time.

From the above relationships, it follows that the tracer concentration $C_{VOI}(t)$ in a given VOI is defined as set forth in Equation (1), which is repeated below:

$$C_{VOI}(t) = F_t \int_0^t C_a(\tau) R(t-\tau) d\tau \qquad \text{Eq. (1)}$$

From Equation (1), it follows that the value of the residue function at t=0 is proportional to the blood flow $F_t$ through the tissue.

In general, Equation (1) is solved for the flow Ft and the residue function R(t) using deconvolution. In one embodiment, a model independent technique known as singular value decomposition (SVD) is used to determine the flow $F_t$ and the shape of the residue function R(t), as described below. It is understood that a variety of other deconvolution approaches cab be used.

For arterial and VOI concentrations measured at equally spaced times $t_1, t_2, \ldots, t_N$, where for small time intervals the residue function and arterial input function values are constant, the convolution of Equation (1) can be defined as a matrix equation as shown below in Equation (7):

$$C(t_j) = \int_0^{t_j} C_a(\tau) R(t-\tau) d\tau \approx \Delta t \sum_{i=0}^{j} C_a(t_i) R(t_j - t_i) \qquad \text{Eq. (7)}$$

or $$\Delta t \begin{pmatrix} C_a(t_1) & 0 & \ldots & 0 \\ C_a(t_2) & C_a(t_1) & \ldots & 0 \\ \ldots & \ldots & \ldots & \ldots \\ C_a(t_N) & C_a(t_{N-1}) & \ldots & C_a(t_1) \end{pmatrix} \begin{pmatrix} R(t_1) \\ R(t_2) \\ \ldots \\ R(t_N) \end{pmatrix} = \begin{pmatrix} C_{br}(t_1) \\ C_{br}(t_2) \\ \ldots \\ C_{br}(t_N) \end{pmatrix}$$

In short hand notation, Equation (7) can be defined by Equation (8):

$$A \cdot b = c \qquad \text{Eq.(8)}$$

where A corresponds to the arterial input function values, b corresponds to the elements of $R(t_j)$ for $j=1,2,\ldots,N$, and c corresponds to the VOI tracer concentrations.

In accordance with SVD techniques, matrices V, W and $U^T$ are constructed such that the inverse of A in Equation (8) ($A^{-1}$) is as follows:

$$A^{-1} = V \cdot W \cdot U^T \qquad \text{Eq.(9)}$$

In general, in SVD the diagonal elements in matrix W are zero or close to zero corresponding to linear equations in Equation (8) that are close to being linear combinations of each other. Since the equations in Equation 7 are close to being linear equations of each other, the data samples are made at times where changes in arterial or VOI concentration over time are small relative to the noise. Thus, elements in matrix A that cause the solution b to oscillate or become meaningless can be identified to minimize these effects on the solution for b, i.e., R(t). Diagonal elements in matrix W below a predetermined threshold can be eliminated (by setting to zero). The result b for the residue function is the best possible solution for a least square fit. A flow map can then be computed from the residue function.

It is understood that a variety of alternative techniques can be used to derive the residue function. Exemplary techniques include so-called model dependent and model independent deconvolution techniques. As known to one of ordinary skill in the art, model dependent techniques assume a specific expression or shape, e.g., exponential, for the residue function and model independent techniques determine the flow and residue function using nonparametric deconvolution. Exemplary model independent techniques include transforms using convolution theorems for the Fourier, Z, or Laplace transforms and algebraic techniques that use matrix equations.

A variety of optical/paramagnetic solutions can be used to provide concentration information and MRI imaging. Exemplary contrast agents include Indocyanine Green (ICG), fluorescein isothiocyanate, silver compounds such as silver nitrate, rose bengal, nile blue and Evans Blue, Q-Switch™, (a dye made by Kodak, Inc.), Sudan III, Sudan Black B and India Ink. Exemplary MRI contrast agents include gadopentetate dimeglumine (Gd-DTPA, Magnevist), gadodiamide (Omniscan), Gadoteridol (ProHance), Gadobutrol (Gadovist), Gd-DO3A (Dotarem), and SHU-555A (Resovist). To provide an optical/paramagnetic solution, one or more optical contrast agents are combined with one or more paramagnetic agents to provide a suitable optical/paramagnetic solution. Possible solutions include a mixture of ICG and Gd-DTPA or ICG and any other MRI contrast agent.

One suitable optical/paramagnetic solution is a mixture of ICG and Gd-DTPA. In an exemplary embodiment, a solution of 0.125 mg/ml ICG and 457.3 mg mg/ml Gd-DTPA is provided. This solution can be produced by dissolution of ICG in sterile water for injection to a concentration of about 5 mg/ml, which is then followed by dilution into full strength Gd-DTPA, which can be provided as Magnevist in a 25:975 ratio. This solution is stable for about three hours after preparation.

It is understood each particular solution can have an associated protocol. For example, The ICG/Gd-DTPAsolution described above should be prepared and stored in rubber stoppered glass vials, administered through a 0.22 micrometer filter, and injected with a plastic syringe.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for determining quantitative blood perfusion indices, comprising:
   administering a bolus containing an optical contrast agent and an MRI (Magnetic Resonance Imaging) contrast agent;
   determining an arterial input function from optical contrast agent concentration samples after the bolus was administered;
   determining a tissue function from MRI contrast agent samples in a tissue volume of interest, wherein the contrast optical agent concentration samples and the MRI contrast agent concentration samples are correlated in time;
   determining at least one quantitative perfusion index from the arterial input function and the tissue function.

2. The method according to claim 1, wherein the optical contrast agent includes ICG (Indocyanine Green).

3. The method according to claim 1, wherein the MRI contrast agent includes Gd-DTPA (Gadopentetate dimeglumine pentaacetic acid).

4. The method according to claim 1, further including deconvolving an MR signal-time curve from the arterial input function and the tissue function to derive the at least one quantitative perfusion index.

5. The method according to claim 4, further including using SVD (Singular Value Decomposition) to deconvolve the MR signal time curve.

6. The method according to claim 4, further including computing a flow map or a blood volume map.

7. The method according to claim 6, further including determining a residue function from the arterial input function and the tissue function and using the residue function to compute the flow map.

8. The method according to claim 1, further including using optical densitometry to determine the optical contrast agent concentration.

9. The method according to claim 1, further including taking blood samples to determine the optical contrast agent concentration.

10. A method for determining quantitative perfusion indices, comprising:
    administering a bolus containing an optical contrast agent and an MRI (Magnetic Resonance Imaging) contrast agent;
    determining an arterial input function $C_a(t)$ from the optical contrast agent;
    determining a tissue function $C_{VOI}(t)$ from the MRI contrast agent;
    deconvolving an MR signal-time curve from the arterial input function $C_a(t)$ and the tissue function $C_{VOI}(t)$ based on $$C_{VOI}(t) = F_t \int_0^t C_a(\tau) R(t-\tau) d\tau,$$

where R(t) is a residue function describing the fraction of MRI contrast agent at time t, and $F_t$ represents tissue flow.

11. The method according to claim 10, further including using SVD (Singular Value Decomposition) to deconvolve the MR signal-time curve.

12. The method according to claim 10, wherein the optical contrast agent includes ICG (Indocyanine Green) and the MRI contrast agent includes GDA (gadopentate dimefluminepentaacetic acid).

13. The method according to claim 10, wherein the bolus comprises about 0.125 mg/ml ICG (Indocyanine Green) and about 457 mg mg/ml GDA (gadopentate dimefluminepentaacetic acid).

14. A bolus solution for intravascular injections comprising:
    an optical contrast agent including Idocyanine Green; and
    an MRI (Magnetic Resonance Imaging) contrast agent including gadoglumine pentaacetic acid.

15. The solution according to claim 14, wherein the Indocyanine Green has a concentration ranging from about 0.01 to 50% by weight based on the total weight of the composition.

16. The solution according to claim 14, wherein the gadoglumine pentaacetic acid has a concentration ranging from about 0.001M to about 0.5M.

17. The solution according to claim 14, wherein the optical contrast agent can provide an arterial input function and the MRI (Magnetic Resonance Imaging) contrast agent can provide a tissue function.

* * * * *

UNITED STATES PATENT AND TRADEMARK OFFICE
CERTIFICATE OF CORRECTION

PATENT NO. : 6,542,769 B2
DATED : April 1, 2003
INVENTOR(S) : Schwamm et al.

It is certified that error appears in the above-identified patent and that said Letters Patent is hereby corrected as shown below:

Column 4,
Line 24, delete "determines" and replace with -- determine --.

Column 6,
Line 15, delete "cab" and replace with -- can --.

Column 7,
Line 29, delete "understood each" and replace with -- understood that each --.
Line 31, delete "DTPAsolution" and replace with -- DTPA solution --.
Line 54, delete "time;" and replace with -- time; and --.

Column 8,
Line 26, delete "agent;" and replace with -- agent; and --.
Line 51, delete "Idocyanine" and replace with -- Indocyanine --.

Signed and Sealed this

Eighth Day of July, 2003

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,542,769 B2 |
| APPLICATION NO. | : 09/739194 |
| DATED | : April 1, 2003 |
| INVENTOR(S) | : Schwamm et al. |

It is certified that error appears in the above-identified patent and that said Letters Patent is hereby corrected as shown below:

Col. 1, line 11, under STATEMENT REGARDING FEDERALLY SPONSORED RESEARCH, delete "Not Applicable." and replace with -- This invention was made with Government support under Grant No. DAMD17-99-2-9001 awarded by the U.S. Department of the Army. The Government has certain rights in this invention. --.

Signed and Sealed this

Twenty-eighth Day of July, 2009

JOHN DOLL
*Acting Director of the United States Patent and Trademark Office*